(12) United States Patent
Montanari et al.

(10) Patent No.: US 9,247,941 B2
(45) Date of Patent: Feb. 2, 2016

(54) CELLULOSE-CONTAINING MEDICAL DEVICE HAVING A MULTI-LAYER STRUCTURE PRODUCED WITHOUT ADHESIVE

(75) Inventors: Suzelei Montanari, Trevoux (FR); Aurelie Serrero, Lyons (FR)

(73) Assignee: Sofradim Production (FR)

( * ) Notice: Subject to any disclaimer, the term of this patent is extended or adjusted under 35 U.S.C. 154(b) by 392 days.

(21) Appl. No.: 13/695,493

(22) PCT Filed: Apr. 28, 2011

(86) PCT No.: PCT/IB2011/001505
§ 371 (c)(1),
(2), (4) Date: Jan. 11, 2013

(87) PCT Pub. No.: WO2011/135463
PCT Pub. Date: Nov. 3, 2011

(65) Prior Publication Data
US 2013/0103076 A1    Apr. 25, 2013

Related U.S. Application Data

(60) Provisional application No. 61/329,875, filed on Apr. 30, 2010.

(51) Int. Cl.
*A61F 13/00* (2006.01)
*A61B 17/08* (2006.01)
*A61L 15/28* (2006.01)
*A61L 15/42* (2006.01)

(52) U.S. Cl.
CPC .............. *A61B 17/08* (2013.01); *A61L 15/28* (2013.01); *A61L 15/425* (2013.01); *A61L 2400/04* (2013.01)

(58) Field of Classification Search
CPC ...... A61B 17/08; A61L 15/28; A61L 15/425; A61L 2400/04; A61F 13/02; A61F 13/0203
USPC ..................... 602/41–59; 134/26; 606/213
See application file for complete search history.

(56) References Cited

U.S. PATENT DOCUMENTS

| | | | | |
|---|---|---|---|---|
| 4,063,018 A | * | 12/1977 | Ohnaka et al. | 536/98 |
| 5,631,078 A | * | 5/1997 | Ellery | B41M 7/0027 428/195.1 |
| 6,083,582 A | * | 7/2000 | Chen | C08B 15/08 428/34.8 |
| 6,962,714 B2 | * | 11/2005 | Hei et al. | 424/405 |
| 2003/0073663 A1 | * | 4/2003 | Wiseman | A61K 31/665 514/54 |
| 2007/0213522 A1 | | 9/2007 | Harris et al. | |
| 2011/0070288 A1 | * | 3/2011 | Andjelic | A61K 38/363 424/445 |

FOREIGN PATENT DOCUMENTS

| | | | |
|---|---|---|---|
| EP | 0 396 344 A2 | | 11/1990 |
| EP | 0 815 881 A2 | | 1/1998 |
| GB | 748 423 A | | 5/1956 |
| WO | WO 2006/042287 A2 | | 4/2006 |

OTHER PUBLICATIONS

Heines, John Mercer and Mercerization, 1844, Sep. 1944, Journal of Chemical Education, 21 (9), p. 430.*

(Continued)

*Primary Examiner* — Kim M Lewis

(57) ABSTRACT

Implants include a film layer containing cellulose secured to a surface of the porous layer that also contains cellulose, wherein the film layer is secured to the porous cellulose without the use of an adhesive.

19 Claims, 1 Drawing Sheet

(56) References Cited

OTHER PUBLICATIONS

International Search Report corresponding to International Application No. PCT/IB2011/001505, date of completion was Oct. 14, 2011 and date of mailing was Oct. 28, 2011; (3 Pages).

Uraki et al., "Honeycomb-like Architecture Produced by Living Bacteria", vol. 69, No. 1, Mar. 30, 2007, pp. 1-6.

E.T.N. Bisanda: "The Effect of Alkali Treatment on the Adhesion Characteristics of Sisal Fibres", Applied Composite Materials, vol. 7, Jan. 1, 2000; pp. 331-339.

\* cited by examiner

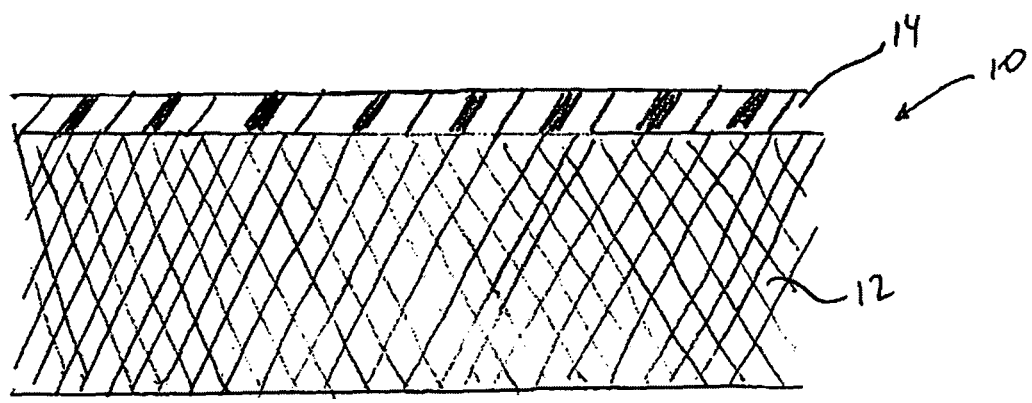

CELLULOSE-CONTAINING MEDICAL DEVICE HAVING A MULTI-LAYER STRUCTURE PRODUCED WITHOUT ADHESIVE

CROSS-REFERENCE TO RELATED APPLICATIONS

This application is a U.S. National Stage Application filed under 35 U.S.C. §371(a) of International Application No. PCT/IB2011/001505 filed Apr. 28, 2011, which claims the benefit of and priority to U.S. Provisional Patent Application Ser. No. 61/329,875 filed Apr. 30, 2010, the entire contents of which are incorporated by reference herein.

BACKGROUND

1. Technical Field

The present disclosure relates to medical devices which include a porous cellulose-containing substrate having a cellulose-containing film secured thereto without the use of an adhesive.

2. Background of Related Art

In situ hemostatic therapy has primarily focused on the transformation of precursor solutions into solids within a patient's body. Transformations have been achieved by a variety of means, including precipitation, polymerization, crosslinking, and desolvation. However, significant limitations exist when using solutions for in situ hemostatic therapy. Solutions of low viscosity may flow away and be cleared from an application site before transformation and solidification occurs. Furthermore, formulation of the solutions may be complex, as preparation of precursor solutions typically requires reconstitution of the precursors, or, when the solutions are stored frozen, thawing.

Therefore it would be desirable to provide in situ hemostatic therapy which includes implantable devices combined with dry materials that are activated by the presence of aqueous physiological fluids. The combination of an implantable device with dry materials ensures the situ hemostatic therapy occurs at the site of implantation.

SUMMARY

A process is contemplated by the present disclosure wherein a film layer that contains cellulose is approximated to a porous layer that contains cellulose and the approximated film layer and porous layer are contacted with a basic solution or a suitable solvent which causes the cellulose fibers to swell to join the film layer and porous layer to form a multi-layered implant without the use of an adhesive.

An aspect of the present invention is a process comprising:
  approximating a film layer comprising cellulose and a porous layer comprising cellulose;
  contacting the approximated film layer and porous layer with a solvent suitable for swelling cellulose to join the film layer and porous layer to form a multi-layered substrate without the use of an adhesive.

In embodiments, the process further comprises oxidizing the multi-layered substrate.

In embodiments, contacting the approximated film layer and porous layer with a solvent suitable for swelling cellulose comprises contacting the approximated film layer and porous layer with a basic solution including a base selected from the group consisting of sodium hydroxide, potassium hydroxide, ammonia, or combinations thereof.

In embodiments, oxidizing comprises exposing the multi-layered substrate to an oxidation medium. For example, oxidizing comprises exposing the multi-layered substrate to nitrogen dioxide dissolved in densified carbon dioxide. In embodiments, oxidizing comprises exposing the multi-layered substrate to densified fluid selected from the group consisting of nitrogen dioxide and carbon dioxide. For example, the densified fluid is a supercritical fluid. In embodiments, the film layer is approximated to a cellulose textile made at least in part of fibers comprising cellulose.

In embodiments, the process further comprises washing the multi-layered substrate to remove the solvent.

In embodiments, the process further comprises sterilizing the multi-layered substrate.

Another aspect of the invention is a process comprising:
  securing a film layer comprising cellulose to a surface of a porous layer comprising cellulose in the presence of a cellulose-solubilizing solvent to form a multi-layered implant;
  washing the multi-layered implant to remove excess solvent, if any;
  drying the washed multi-layered implant; and
  oxidizing the dried multi-layered implant in the presence of nitrogen dioxide. In embodiments, the film layer is adhered to a textile made at least in part of fibers comprising cellulose. In embodiments, the process further comprises sterilizing the multi-layered implant.

According to another embodiment of the present disclosure, a medical device includes a film layer containing cellulose secured to a surface of a porous layer that also contains cellulose, wherein the film layer is secured to the porous layer without the use of an adhesive. In embodiments, the film layer consists essentially of cellulose. In embodiments, the porous layer comprises a textile made at least in part of fibers comprising cellulose. In embodiments, the porous layer comprises a textile made entirely of fibers consisting essentially of cellulose. In embodiments, the film layer comprising fibers comprising cellulose, cellulose fibers of the porous layer and the film layer are physically intertwined. In embodiments, the film layer is bound to a surface of the porous layer by intertwined cellulose fibers of the film layer and the porous layer.

Another aspect of the invention relates to a medical device comprising:
  a porous layer comprising cellulose; and
  a film layer comprising cellulose bound to a surface of the porous layer;
  wherein cellulose fibers of the porous layer and the film layer are physically intertwined.

BRIEF DESCRIPTION OF THE DRAWINGS

The accompanying drawing, which is incorporated in and constitutes a part of this specification, illustrates embodiments of the disclosure and, together with a general description of the disclosure given above, and the detailed description of the embodiments given below, serves to explain the principles of the disclosure.

FIG. 1 is a schematic cross-sectional view of a porous substrate layer having a cellulose film secured thereon as described in at least one of the embodiments in the present disclosure.

DETAILED DESCRIPTION OF THE EMBODIMENTS

Hemostatic implants in accordance with the present disclosure, also referred to herein as medical devices, multi-layered substrates or multi-layered structures, include a porous cellulose substrate having a cellulose film applied thereto. With reference to FIG. 1, a hemostatic implant is shown as a multi-layered structure 10 having a porous layer 12 secured to a film layer 14. During use, the implant is oriented with porous layer 12 being applied closer to the tissue and film layer 14 being applied further from the tissue, thus allowing porous layer 12 to absorb fluids and film layer 14 to prevent the fluids from spreading. In embodiments, portions of the implant may be distinguishable from one another by the addition of contrast dyes, surface texturing, coloring or other visual cues.

The implant may be used for a variety of surgical and wound applications. Examples include closing and healing visceral wall defects and incisions, including incisions due to the removal of tumors, wounds, anastomoses, and fistulae. The implant can improve the healing of gastro-intestinal anastomosis and may provide an effective approach to the management and prevention of fistula. The implant may also prevent complications of polypectomy (e.g., bleeding and perforation). In embodiment, the implant may be reinforced with a mesh for the treatment of inguinal hernia and incisional hernia. The implant, in a dried state, can be from about 0.2 mm to about 20 mm thick. In embodiments, the thickness of the entire implant may be between about 0.2 mm and 5 mm.

The implant may be formed by physically approximating a pre-formed film layer with a pre-formed porous layer. Approximating a pre-formed film layer with a pre-formed porous layer may be achieved by any technique within the purview of those skilled in the art. In embodiments, approximating a pre-formed film layer with a pre-formed porous layer includes hydrating the film layer 14, such as for example, in de-ionized water, and spreading out the film layer 14 within a reactor vessel (not shown) having a non-reactive smooth surface (e.g., glass, PVC, silicone or the like). The porous layer 12 is then positioned over and in contact with film layer 14 without the use of any adhesive or other materials suitable for securing the porous layer 12 to the film layer 14.

The approximated film layer 14 and the porous layer 12 are then contacted with a solvent capable of swelling or solubilizing cellulose. Contacting with the solubilizing solvent may be achieved by any technique within the purview of those skilled in the art. In embodiments, a basic solution is simply poured into the reaction vessel in an amount sufficient to cover the interface of the approximated film and porous layers. It should of course be understood that the entire thickness of porous layer 12 may be submerged or that porous layer 12 may be only partially submerged in the basic solution. The solvent may be any composition capable of swelling or solubilizing the cellulose fibers of the porous layer and the porous layer. In embodiments, when a basic medium is used, the basic medium may be an aqueous, alcohol or mixed aqueous/alcohol solution of sodium hydroxide, potassium hydroxide, or a combination thereof. Ammonia in liquid or gaseous phase may also be used. In an embodiment, the fibers of the porous and film layers may be solubilized or swollen by an organic-based medium such as N-methylmorpholine-N-oxide or the like.

Without wishing to be bound by any theory, it is believed that the basic solution or solvent causes the cellulose fibers of the porous layer and film layer to swell thereby permitting the fibers of the two layers to become intertwined such that the two layers are physically bound together without the use of any adhesive.

It has been found that swelling of the porous layer, particularly in textile form, is an important factor in obtaining the desired structure. For example, if the swelling penetrate too deeply into the porous layer, the cellulose fibers may become irrevocably modified and the porous layer will shrink and become stiff after drying—even when the porous layer is thoroughly washed prior to drying. The shrinking and/or stiffening may be overcome by limiting the swelling of the porous cellulose layer. In an embodiment, one means of limiting swelling is to reduce the hydroxide concentration in an aqueous solution. However, when the sodium hydroxide concentration is decreased, the resulting decrease in swelling also causes a decrease or even lack of attachment between the porous layer and the film layer. It has been found that the optimal concentration of sodium hydroxide in an aqueous solution is in the range of 1.5N to 2.5N, preferably 2N.

The swelling may also be limited by modifying the interactions between the cellulose of the porous layer and the alkaline medium. In an embodiment, an alcohol such as ethanol and the like is used as the medium either alone or in combination with water to dissolve the sodium hydroxide. When a mixture of water and alcohol is used to dissolve the hydroxide, the ratio of water/alcohol (w/w) is preferably in the range of between 3/97 and 20/80, more preferably in the range of 5/95 and 15/85, and most preferably about 10/90.

The resulting multi-layered structure 10, when joined with use of a basic solution, is then removed from the solution and washed to remove any residual basic solution. Washing may be achieved by any technique within the purview of those skilled in the art. For example, the multi-layered structure 10 may simply be flushed with de-ionized water or other suitable washing medium such as an alcohol and/or a mixture of water and an alcohol. The pH of the effluent may be monitored to determine when sufficient washing has been achieved. Other suitable washing methods will be readily envisioned by those skilled in the art.

The multi-layered structure 10 is dried. Drying may be achieved by any technique within the purview of those skilled in the art. For example, the washed multi-layered structure 10 may be dried by heating to cause evaporation of the washing medium. As another example, the washed multi-layered structure 10 may be dried by freeze-drying to remove the washing medium. Other suitable drying methods will be readily envisioned by those skilled in the art. In embodiments, drying may be accomplished by air drying for a period of hours or several days or any other methods by varying time, temperature and pressure of the drying conditions. Once the multi-layered structure 10 is sufficiently dried, the multi-layered structure 10 may be trimmed to any desired size and shape to form suitable implants.

Cellulose in the multi-layered structure 10 may be oxidized by any technique within the purview of those skilled in the art. For example, cellulose in the multi-layered structure 10 may be oxidized by exposing the multi-layered structure 10 to nitrogen dioxide in densified form. The nitrogen dioxide may be dissolved in densified carbon dioxide. The multi-layered structure 10 may be exposed to the oxidizing medium for a period of time from about 10 minutes to about 10 hours at a temperature of from about 20° C. to about 60° C. and at a pressure of from about 20 bars to about 250 bars. Methods for oxidizing cellulose materials using densified fluids, for example selected from the group consisting of nitrogen dioxide and carbon dioxide, are disclosed, for example in U.S. Patent Publication No. 2008/0194805, the entire disclosure which is incorporated by reference herein.

Film layer 14 may be formed from any composition containing cellulose. The cellulose in the film layer may be oxidized or not oxidized. Film layer 14 should contain sufficient cellulose to provide adequate cellulose molecules at the surface of the film layer to permit bonding of the film layer to cellulose molecules at the surface of the porous layer. In embodiments, porous layer may contain from about 5% to about 100% cellulose by weight, in other embodiments from about 20% to about 90% cellulose by weight, in yet other embodiments from about 50% to about 80% cellulose by weight. In addition to cellulose, the film layer may contain any natural or synthetic biocompatible material. The film layer may also contain conventional additives such as plasticizers, colorants or the like.

In embodiments, porous layer 12 is made at least in part from fibers containing un-oxidized or oxidized cellulose. Porous layer 12 of the implant may have openings or pores over at least a portion of a surface thereof.

Suitable materials for forming porous layer 12 include, but are not limited to fibrous structures (e.g., two-dimensional and three-dimensional knitted structures, woven structures, non-woven structures, etc.) and/or foams (e.g., open or closed cell foams). In embodiments, the pores may be in sufficient number and size so as to interconnect across the entire thickness of porous layer 12. Woven fabrics, knitted fabrics and open cell foam are illustrative examples of structures in which the pores can be in sufficient number and size so as to interconnect across the entire thickness of porous layer 12. In embodiments, the pores do not interconnect across the entire thickness of porous layer 12. Closed cell foam or fused non-woven materials are illustrative examples of structures in which the pores may not interconnect across the entire thickness of porous layer 12. The pores of the foam porous layer 12 may span across the entire thickness of porous layer 12. In yet other embodiments, the pores do not extend across the entire thickness of the porous layer 12, but rather are present at a portion of the thickness thereof. In embodiments, the openings or pores are located on a portion of the surface of porous layer 12, with other portions of porous layer 12 having a non-porous texture. Where porous layer 12 is fibrous, the fibers may be filaments or threads suitable for knitting or weaving or may be staple fibers, such as those frequently used for preparing non-woven materials.

Where porous layer 12 is fibrous, porous layer 12 may be formed using any method suitable to forming fibrous structures, including but not limited to knitting, weaving, non-woven techniques, wet-spinning, electro-spinning, extrusion, co-extrusion, and the like. Suitable techniques for making fibrous structures are within the purview of those skilled in the art. In embodiments, the textile has a three dimensional structure, such as the textiles described in U.S. Pat. Nos. 7,021,086 and 6,443,964, the entire disclosure of each of which is incorporated by reference herein.

In embodiments, porous layer 12 is made from fibers that are made entirely from cellulose. In other embodiments, porous layer 12 is made from fibers that are made from a composition containing cellulose and another biocompatible material. In yet other embodiments, porous layer 12 is made from a combination of fibers of different composition, e.g., some fibers made from a composition that includes cellulose (either 100% cellulose or a combination of cellulose and another material) and some fibers made from some other natural or synthetic biocompatible material. Porous layer 12 should contain a sufficient number of cellulose-containing fibers to provide adequate cellulose molecules at the surface of the porous layer to permit bonding of the porous layer to cellulose molecules at the surface of the film layer. In embodiments, porous layer may be made from fibers that contain from about 5% to about 100% cellulose by weight, in other embodiments from about 20% to about 90% cellulose by weight, in yet other embodiments from about 50% to about 80% cellulose by weight. In embodiments where porous layer 12 is made from a combination of cellulose-containing fibers in combination with fibers made from some other natural or synthetic biocompatible material, the porous layer may contain from about 5% to about 100% by weight of cellulose-containing fibers, in other embodiments from about 20% to about 90% by weight of cellulose-containing fibers, in yet other embodiments from about 50% to about 80% by weight of cellulose-containing fibers. The fibers of the porous layer may also contain conventional additives such as plasticizers, colorants or the like.

Where porous layer 12 is foam, porous layer 12 may be formed using any method suitable to forming a foam or sponge including, but not limited to lyophilization or freeze-drying of a composition. The foam may be cross-linked or non-cross-linked, and may include covalent or ionic bonds. Suitable techniques for making foams are within the purview of those skilled in the art. The foam should contain sufficient cellulose to provide adequate cellulose molecules at the surface of the porous layer to permit bonding of the porous layer to cellulose molecules at the surface of the film layer. In embodiments, the foam may contain from about 5% to about 100% cellulose by weight, in other embodiments from about 20% to about 90% cellulose by weight, in yet other embodiments from about 50% to about 80% cellulose by weight. In addition to cellulose, the foam may contain any natural or synthetic biocompatible material. The foam may also contain conventional additives such as plasticizers, colorants or the like.

The size of the pores in porous layer 12 can be from about 2 μm to about 300 μm, in embodiments from about 50 μm to about 150 μm. It is envisioned that the pores may be arranged in any manner. For example, the pores may be configured in a random or uniform manner. In some embodiments, the pores may be formed with the use of copper alginate to create a honey-comb shaped porous layer 12. In still other embodiments, the pores may be configured to create a gradient in the porous layer 12. The gradient may further enhance the ability of porous layer 12 to absorb the physiologic fluid.

Materials for use as porous layer 12 include oxidized cellulose hemostat materials commercially available under the trade name SURGICEL®. Methods for preparing oxidized cellulose hemostat materials are disclosed, for example in U.S. Pat. Nos. 3,364,200; 4,626,253; 5,484,913; and 6,500,777, the entire disclosure of each of which is incorporated by reference herein.

In addition to providing hemostasis, the present implants may further be use for delivery of a bioactive agent. Thus, in some embodiments, at least one bioactive agent may provided in or on porous layer 12 or film layer 14. The agents may be freely admixed with the precursors or may be tethered to one or more of the layers through any variety of chemical bonds. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present implant in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents also include viruses and cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

It will be appreciated that of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A process for forming a medical device comprising:
   approximating a film layer comprising cellulose fibers and a porous layer comprising cellulose fibers;
   contacting the approximated film layer and porous layer with a solvent suitable for swelling cellulose to join the film layer and porous layer to form the medical device as a multi-layered substrate without the use of an adhesive, wherein the medical device is an implantable hemostat and the film layer is bound to a surface of the porous layer by intertwined cellulose fibers of the film layer and the porous layer.

2. A process according to claim 1, further comprising oxidizing the multi-layered substrate.

3. A process according to claim 2, wherein oxidizing comprises exposing the multi-layered substrate to an oxidation medium.

4. A process according to claim 3, wherein oxidizing comprises exposing the multi-layered substrate to nitrogen dioxide dissolved in densified carbon dioxide.

5. A process according to claim 3, wherein oxidizing comprises exposing the multi-layered substrate to densified fluid selected from the group consisting of nitrogen dioxide and carbon dioxide.

6. A process according to claim 5, wherein the densified fluid is a supercritical fluid.

7. A process according to claim 1, wherein contacting the approximated film layer and porous layer with a solvent suitable for swelling cellulose comprises contacting the approximated film layer and porous layer with a basic solution including a base selected from the group consisting of sodium hydroxide, potassium hydroxide, ammonia, or combinations thereof.

8. A process according to claim 1, further comprising washing the multi-layered substrate to remove the solvent.

9. A process according to claim 1, further comprising sterilizing the multi-layered substrate.

10. The process of claim 1, wherein contacting the approximated film layer and porous layer with a solvent suitable for swelling cellulose comprises contacting the approximated film layer and porous layer with a solution of sodium hydroxide at a concentration from 1.5N to 2.5N.

11. The process of claim 10, wherein the solution of sodium hydroxide includes a ratio of water and alcohol ranging from about 3/97 to 20/80 (w/w).

12. The process of claim 1, wherein contacting the approximated film layer and porous layer with a solvent suitable for swelling cellulose comprises contacting the approximated film layer and porous layer with a solution of sodium hydroxide at a concentration of 2N.

13. The process of claim 12, wherein the solution of sodium hydroxide includes a ratio of water and alcohol ranging from about 10/90 (w/w).

14. The process of claim 1, wherein the film layer comprising cellulose and the porous layer comprising cellulose are both pre-formed prior to approximating.

15. A medical device comprising:
 a porous layer comprising cellulose fibers; and
 a film layer comprising cellulose fibers secured to a surface of the porous layer, wherein the film layer is secured to the porous layer without the use of an adhesive, wherein the medical device is an implantable hemostat and the film layer is bound to a surface of the porous layer by intertwined cellulose fibers of the film layer and the porous layer.

16. A medical device according to claim 15, wherein the film layer consists essentially of cellulose.

17. A medical device according to claim 15 wherein the porous layer comprises a textile made entirely of fibers consisting essentially of cellulose.

18. The medical device of claim 15, wherein the implantable hemostat consists essentially of the porous layer comprising cellulose and the film layer comprising cellulose.

19. The medical device of claim 18, wherein the porous layer comprising cellulose is configured to absorb bodily fluids upon implantation and the film layer comprising cellulose is configured to prevent the absorbed bodily fluids from spreading.

* * * * *